US008685646B2

(12) United States Patent
Battersby et al.

(10) Patent No.: US 8,685,646 B2
(45) Date of Patent: Apr. 1, 2014

(54) METHODS AND REAGENTS FOR SHORTENING INCUBATION TIMES IN HYBRIDIZATION ASSAYS

(75) Inventors: Thomas Battersby, El Cerrito, CA (US); Mark Baumeister, Richmond, CA (US); Jesse Brooks, Oakland, CA (US); Felix Kleshik, Berkeley, CA (US); Stacey Tam, Walnut Creek, CA (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 224 days.

(21) Appl. No.: 13/133,275

(22) PCT Filed: Dec. 18, 2009

(86) PCT No.: PCT/US2009/068629
§ 371 (c)(1),
(2), (4) Date: Jun. 7, 2011

(87) PCT Pub. No.: WO2010/080566
PCT Pub. Date: Jul. 15, 2010

(65) Prior Publication Data
US 2011/0236997 A1 Sep. 29, 2011

Related U.S. Application Data

(60) Provisional application No. 61/138,601, filed on Dec. 18, 2008.

(51) Int. Cl.
*C12Q 1/68* (2006.01)
(52) U.S. Cl.
USPC .......................................... 435/6.11
(58) Field of Classification Search
None
See application file for complete search history.

(56) References Cited

U.S. PATENT DOCUMENTS

| | | | |
|---|---|---|---|
| 4,302,204 | A | 11/1981 | Wahl et al. |
| 5,093,232 | A | 3/1992 | Urdea et al. |
| 5,124,246 | A | 6/1992 | Urdea et al. |
| 5,512,436 | A | 4/1996 | Stone |
| 5,624,802 | A | 4/1997 | Urdea et al. |
| 5,635,352 | A | 6/1997 | Urdea et al. |
| 5,681,697 | A | 10/1997 | Urdea et al. |
| 5,681,702 | A | 10/1997 | Collins et al. |
| 5,780,610 | A | 7/1998 | Collins et al. |
| 5,853,986 | A | 12/1998 | Petrie et al. |
| 7,150,966 | B2 | 12/2006 | Nikilorov |
| 2004/0234964 | A1 | 11/2004 | Cole et al. |
| 2007/0015188 | A1 | 1/2007 | Luo et al. |

FOREIGN PATENT DOCUMENTS

WO 2009041917 4/2009

OTHER PUBLICATIONS

Kern, et al.; An Enhanced-Sensitivity Branched-DNA Assay for Quantification of Human Immunodeficiency Virus Type 1 RNA in Plasma; Journal of Clinical Microbiology, 34(12): 3196-3202, (1996).
Tan, et al.; Sulfonic Acid Polymers Are Potent Inhibitors of HIV-1 Induced Cytopathogenicity and the Reverse Transcriptases of Both HIV-1 and HIV-2; Biochimica et Biophysica Acta, 1181: 183-188, (1993).
Volkova, et al.; Water-Soluble Nonstoichiometric Polyelectrolyte Complexes of Chitosan With a Polystyrenesulfonate Anion, Polymer Science, 50(9): 971-976, (2008).
Tan, et al.; Nucleic Acid Helix Stability: Effects of Salt Concentration, Cation Valence and Size, and Chain Length, Biophysical Journal, 90: 1175-1190, (2006).
International Search Report for PCT/US09/068629 dated Mar. 2, 2010.
Zheng et al., "Sensitive and Quantitative Measurement of Gene Expression Directly from a Small Amount of Whole Blood", 2006, Clinical Chemistry 52:7, Molecular Diagnostics and Genetics, pp. 1294-1302.
Collins et al., "A Branched DNA Signal Amplification Assay for Quantification of Nucleic Acid Targets Below 100 Molecules/ml", Nucleic Acids Research, 1997, vol. 25, No. 15, pp. 2979-2984.
Schildkraut et al., "Dependence of the Melting Temperature of DNA on Salt Concentration", 1965, Biopolymers, vol. 3, pp. 195-208.
Wieder et al., "One Hundred-Fold Acceleration of DNA Renaturation Rates in Solution", 1981, Biopolymers, vol. 20, pp. 1537-1547.
Leary et al.,"Rapid and Sensitive Colorimetric Method for Visualizing Biotin-Labeled DNA Probes Hybridized to DNA or RNA Immobilized on Nitrocellulose: Bio-blots", Jul. 1983, Pro. Natl. Acad. Sci., Genetics, vol. 80, pp. 4045-4049.
Renz et al., "A Colorimetric Method for DNA Hybridization", 1984, Nucleic Acids Research, vol. 12, No. 8, pp. 3435-3444.
Richardson et al., "Biotin and Fluorescent Labeling of RNA using T4 RNA Ligase", 1983, Nucleic Acids Research, vol. 11, No. 18, pp. 6167-6184.
Smith et al., "The Synthesis of Oligonucleotides Containing an Aliphatic Amino Group at the 5' Terminus: Synthesis of Fluorescent DNA Primers for use in DNA Sequence Analysis", 1985, Nucleic Acids Research, vol. 13, No. 7, pp. 2399-2412.
Meinkoth et al., "Hybridization of Nucleic Acids Immobilized on Solid Supports", May 1984, Analytical Biochemsitry,138 (2), pp. 267-284.

*Primary Examiner* — James Martinell

(57) ABSTRACT

The methods and reagents described herein can be used to shorten incubation times in hybridization assays. As demonstrated in the examples, we have identified specific sulfonic acid polymers and hybridization conditions that lead to significantly shorter incubation times (e.g., signals after three hours that are comparable to signals that could traditionally only be obtained after overnight incubation). In some embodiments, shorter incubation times are achieved by adding the sulfonic acid polymer(s) during the hybridization process. Alternatively or additionally, in some embodiments, shorter incubation times are achieved via changes to the hybridizing conditions, e.g., by reducing the hybridization volume, increasing the salt concentration, andor increasing the probe concentration (capture extender probe andor label extender probe).

46 Claims, 2 Drawing Sheets

METHODS AND REAGENTS FOR SHORTENING INCUBATION TIMES IN HYBRIDIZATION ASSAYS

REFERENCE TO RELATED APPLICATIONS

The present application claims priority to U.S. provisional application Ser. No. 61/138,601 filed Dec. 18, 2008, the entire contents of which are herein incorporated by reference.

BACKGROUND

A variety of assays have been developed in the art for detecting the presence, and optionally quantifying the amount, of a target nucleic acid in a sample (e.g., DNA or RNA). For example, a number of polymerase chain reaction (PCR) based assays have been developed that involve an initial step of amplifying a region of the target nucleic acid and then detecting the presence of the amplified product.

A number of hybridization assays have been developed as alternatives to PCR based assays (e.g., see Collins et al., Nucleic Acids Research, (1997) 25:2979-2984 and U.S. Pat. Nos. 5,635,352; 5,124,246; 5,681,697; 5,681,702; 5,780,610 and 5,624,802). Hybridization assays do not rely on amplification of the target nucleic acid. Instead, as illustrated in FIGS. 1 and 2, they rely on a series of complex nucleic acid hybridizations. Individual target nucleic acids are captured on a solid phase using a combination of capture probes. Some of the capture probes are bound to a solid phase (solid phase capture probes), while others are free in solution (capture extender probes). The capture extender probes have two segments. One segment hybridizes to the solid phase capture probe while the other segment hybridizes to a region of the target nucleic acid. Detection of the captured target nucleic acid is achieved using a combination of yet more probes that are free in solution. Label extender probes include segments that hybridize to a region of the target nucleic acid and the preamplifier probe portion of a nucleic acid multimer, respectively. In addition to a preamplifier probe portion, the nucleic acid multimer also includes a multiplicity of amplifier probes that are non-covalently hybridized (e.g., as shown in FIG. 1) or covalently linked (e.g., as shown in FIG. 2). The detection multimers can be branched as shown in FIGS. 1 and 2 or they can be linear. Finally, labeled oligonucleotides that hybridize to the amplifier probes of the nucleic acid multimer allow the captured target nucleic acid to be detected.

Because hybridization assays rely on such a complex and intertwined series of hybridization steps they can take a long time to complete and currently require an overnight incubation. This lengthy incubation period forces the assay to be a two day process. Many clinicians and clinical laboratories that use hybridization assays (e.g., to determine HIV or HCV viral load) would significantly benefit from a one day hybridization assay. There is therefore a need in the art for methods and reagents that shorten incubation times in hybridization assays.

SUMMARY

The methods and reagents described herein can be used to shorten incubation times in hybridization assays. As demonstrated in the examples, we have identified specific sulfonic acid polymers and hybridization conditions that lead to significantly shorter incubation times (e.g., signals after three hours that are comparable to signals that could traditionally only be obtained after overnight incubation). In some embodiments, shorter incubation times are achieved by adding the sulfonic acid polymer(s) during the hybridization process. Alternatively or additionally, in some embodiments, shorter incubation times are achieved via changes to the hybridizing conditions, e.g., by reducing the hybridization volume, increasing the salt concentration, and/or increasing the probe concentration (capture extender probe and/or label extender probe).

CHEMICAL DEFINITIONS

Figure 1:
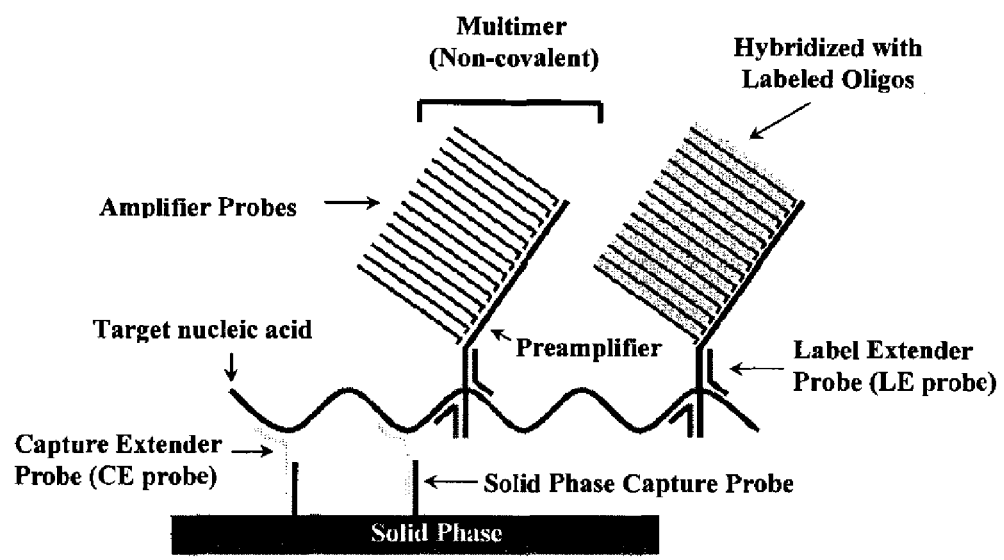
FIG. 1 shows one embodiment of a hybridization assay architecture that may be used according to methods described herein. As shown, this particular assay architecture uses a non-covalent nucleic acid multimer for detection. The non-covalent nucleic acid multimer includes a preamplifier probe that hybridizes to a multiplicity of amplifier probes.

The term "aliphatic" or "aliphatic group", as used herein, denotes a hydrocarbon moiety that may be straight-chain (i.e., unbranched), branched, or cyclic (including fused, bridging, and spiro-fused polycyclic) and may be completely saturated or may contain one or more units of unsaturation, but which is not aromatic. Unless otherwise specified, aliphatic groups contain 1-6 carbon atoms. In some embodiments, aliphatic groups contain 1-4 carbon atoms, and in yet other embodiments aliphatic groups contain 1-3 carbon atoms. Suitable aliphatic groups include, but are not limited to, linear or branched, alkyl, alkenyl, and alkynyl groups, and hybrids thereof such as (cycloalkyl)alkyl, (cycloalkenyl)alkyl or (cycloalkyl)alkenyl.

The term "unsaturated", as used herein, means that a moiety has one or more units of unsaturation.

The term "alkyl," as used herein, refers to a monovalent saturated, straight—or branched—chain hydrocarbon radical derived from an aliphatic moiety containing between one and six carbon atoms by removal of a single hydrogen atom. In some embodiments, alkyl contains 1-5 carbon atoms. In another embodiment, alkyl contains 1-4 carbon atoms. In still other embodiments, alkyl contains 1-3 carbon atoms. In yet another embodiment, alkyl contains 1-2 carbons. Examples of alkyl radicals include, but are not limited to, methyl, ethyl, n-propyl, isopropyl, n-butyl, iso-butyl, sec-butyl, sec-pentyl, iso-pentyl, tert-butyl, n-pentyl, neopentyl, n-hexyl, sec-hexyl, n-heptyl, n-octyl, n-decyl, n-undecyl, dodecyl, and the like.

The term "alkenyl," as used herein, refers to a monovalent group derived from a straight—or branched—chain aliphatic moiety having at least one carbon-carbon double bond by the removal of a single hydrogen atom. In certain embodiments, alkenyl contains 2-6 carbon atoms. In certain embodiments, alkenyl contains 2-5 carbon atoms. In some embodiments, alkenyl contains 2-4 carbon atoms. In another embodiment, alkenyl contains 2-3 carbon atoms. Alkenyl groups include, for example, ethenyl ("vinyl"), propenyl ("allyl"), butenyl, 1-methyl-2-buten-1-yl, and the like.

The term "alkynyl," as used herein, refers to a monovalent group derived from a straight—or branched—chain aliphatic moiety having at least one carbon-carbon triple bond by the removal of a single hydrogen atom. In certain embodiments, alkynyl contains 2-6 carbon atoms. In certain embodiments, alkynyl contains 2-5 carbon atoms. In some embodiments, alkynyl contains 2-4 carbon atoms. In another embodiment, alkynyl contains 2-3 carbon atoms. Representative alkynyl groups include, but are not limited to, ethynyl, 2-propynyl ("propargyl"), 1-propynyl, and the like.

The term "alkylene" refers to a bivalent alkyl group. An "alkylene chain" is a polymethylene group, i.e., —(CH$_2$)$_n$—, wherein n is a positive integer, preferably from 1 to 6, from 1 to 4, from 1 to 3, from 1 to 2, or from 2 to 3.

The terms "cycloalkyl" and "cycloalkenyl", used alone or as part of a larger moiety, refer to a saturated or partially unsaturated cyclic aliphatic monocyclic or bicyclic ring systems, as described herein, having from 3 to 10 members. Cycloalkyl and cycloalkenyl groups include, without limitation, cyclopropyl, cyclobutyl, cyclopentyl, cyclopentenyl, cyclohexyl, cyclohexenyl, cycloheptyl, cycloheptenyl, cyclooctyl, cyclooctenyl, and cyclooctadienyl. In some embodiments, the cycloalkyl has 3-6 carbons.

The term "heteroaryl" refers to a group having 5 to 10 ring atoms, preferably 5, 6, or 9 ring atoms; having 6, 10, or 14π electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. 6-Membered heteroaryl groups include, for example, pyridyl, pyridazinyl, pyrimidinyl, and pyrazinyl. The term "heteroaryl", as used herein, also includes groups in which a heteroaryl ring is fused to one or more aryl, cycloaliphatic, or heterocyclyl rings, where the radical or point of attachment is on the heteroaryl ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be mono- or bicyclic.

DETAILED DESCRIPTION OF VARIOUS EMBODIMENTS

This application refers to a number of documents including patent and non-patent documents. The entirety of each of these documents is incorporated herein by reference.

The methods and reagents described herein can be used to shorten incubation times in hybridization assays. As demonstrated in the examples, we have identified specific sulfonic acid polymers and hybridization conditions that lead to significantly shorter incubation times (e.g., signals after three hours that are comparable to signals that could traditionally only be obtained after overnight incubation). In some embodiments, shorter incubation times are achieved by adding the sulfonic acid polymer(s) during the hybridization process. Alternatively or additionally, in some embodiments, shorter incubation times are achieved via changes to the hybridizing conditions, e.g., by reducing the hybridization volume, increasing the salt concentration, and/or increasing the probe concentration (capture extender probe and/or label extender probe).

Before discussing these methods and reagents in more detail we introduce the various components and steps that are involved in the assays of the present disclosure.

Target Nucleic Acids

In a nucleic acid hybridization assay, a target nucleic acid is detected in a sample via a series of hybridization reactions that occur between a set of complementary nucleic acid probes. As used herein the term "target nucleic acid" refers to one or more single- and/or double-stranded nucleic acid molecules which contain a target nucleotide sequence. In some embodiments, the target nucleic acid is RNA, DNA, or a combination thereof. In certain embodiments the target nucleic acid may include one or more modified nucleotides.

Target nucleic acids may be from a variety of sources including from one or more biological samples. In this context, the term "biological sample" refers to samples isolated from any biological source. For example, biological samples may be obtained from animals such as humans, e.g., from plasma, serum, spinal fluid, semen, lymph fluid, the external sections of the skin, respiratory, intestinal, and genitourinary tracts, tears, saliva, milk, blood cells, tumors, organs, etc. In some embodiments, biological samples may be samples of in vitro cell culture constituents (including conditioned medium resulting from the growth of cells in cell culture medium, putatively virally infected cells, recombinant cells, and cell components). In some embodiments, biological samples may encompass viral nucleic acids, e.g., from hepatitis B virus ("HBV"), hepatitis C virus ("HCV"), hepatitis D virus ("HDV"), human immunodeficiency virus ("HIV"), and the herpes family of viruses, including herpes zoster (chicken pox), herpes simplex virus I & II, cytomegalovirus, Epstein-Barr virus, Herpes VI virus, or any other virus. In some embodiments, biological samples may encompass bacterial nucleic acids, e.g., from bacteria such as *Chlamydia, Mycobacterium tuberculosis*, or any other bacteria. In some embodiments, a target nucleic may be from an environmental sample, e.g., from a soil, water, flora, etc. sample.

In some embodiments, the target nucleic acid is isolated from a biological and/or environmental sample prior to addition to the hybridization assay. In some embodiments, the target nucleic acid is released from the sample by cell lysis and/or chemical extraction. In preferred embodiments, the sample is lysed in a buffer containing salt, detergent, and/or other components that promote sample lysis and release of the target nucleic acid. In some embodiments, the target nucleic acid may be prepared from a sample by standard cloning or amplification methods.

In some embodiments, the target nucleic acid may be further prepared for the hybridization assay by a variety of means including but not limited to the addition of proteinase K/SDS, chaotropic salts, or the like, or phenol/chloroform extraction.

In some embodiments, it may be desired to decrease the average size of the analyte nucleic acids by enzymatic, physical or chemical means. These techniques include but are not limited to restriction enzymes, sonication, and chemical degradation. The fragments may be as small as 0.1 kb, usually being at least 0.5 kb and may be 1 kb or higher. The target sequence is preferably provided in single-stranded form for analysis. Where the sequence is naturally present in single-stranded form, denaturation will not be required. However, where the sequence is present in double-stranded form, the sequence may be denatured. Denaturation can be carried out by various techniques, such as alkali, generally from 0.05 to 0.2 M hydroxide, formamide, salts, chaotropic salts, heat, or combinations thereof.

Target Nucleic Acid Capture

Figure 2:
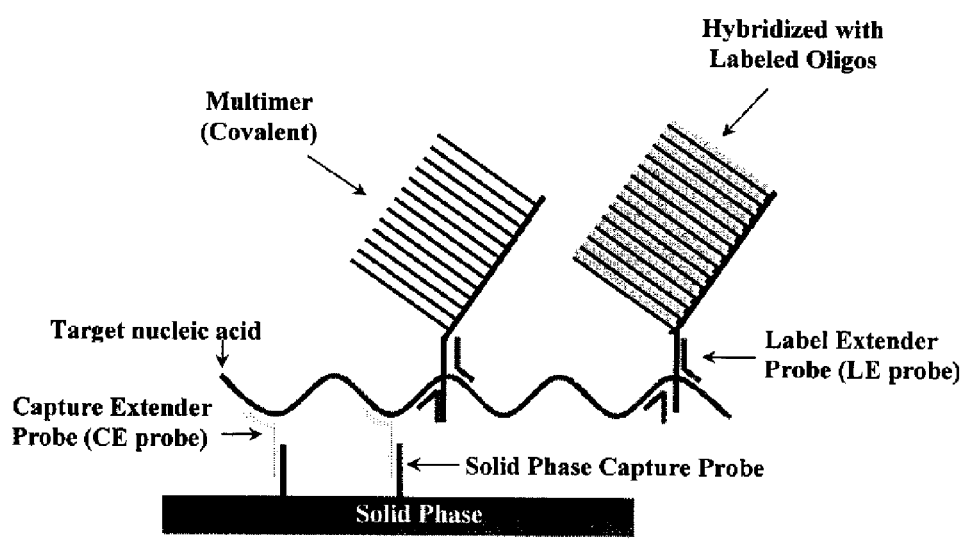
FIG. 2 shows another embodiment of a hybridization assay architecture that may be used according to methods described herein. As shown, this particular assay architecture uses a covalent nucleic acid multimer for detection. The non-covalent nucleic acid multimer includes a preamplifier probe that is covalently linked to a multiplicity of amplifier probes in a branched "comb" architecture.

In the first step of a hybridization assay a single stranded target nucleic acid (prepared as described above) is mixed under hybridization conditions with oligonucleotide probes that hybridize at different sites along the target nucleic acid (FIGS. 1 and 2).

Capture extender (CE) probes function as a bridge between the target nucleic acid and a solid phase and thereby capture the target nucleic acid on the solid phase (FIGS. 1 and 2). In some embodiments, CE probes include a segment that is complementary with a sequence of the target nucleic acid and a segment that is complementary with an oligonucleotide capture probe that is bound to the solid phase. Alternatively, in some embodiments, the CE probes may include one member of a ligand-receptor pair while the solid phase includes the other member of the pair. The affinity of the ligand-receptor pair causes the CE probe to become bound to the solid phase. Examples of such pairs include biotin/avidin, thyroxine/thyroxine-binding globulin, antigen/antibody, carbohydrate/lectin.

Solid phases used in an assay can be particulate (e.g., in the forms of beads), exposed surfaces of porous materials or can be the surface of any of a variety of containers, which include but are not limited to centrifugal tubes, columns, microtiter plate wells, filters, tubing, or other surfaces to which an oligonucleotide capture probe can be bound. When particles are used, they will preferably be of a size in the range of 0.4 to 200 microns, more usually from 0.8 to 4.0 microns. The particles may be any convenient material, such as latex, or glass. In some embodiments, microtiter plates are used as the solid phase. In some embodiments, the solid phase capture probes may be bound to the solid phase via covalent bonds to functional groups on the solid phase surface by known procedures in the art.

Label extender (LE) probes also hybridize to the target nucleic acid via complementary sequences. Similar to the CE probes, the LE probes are bifunctional. In addition to binding the target nucleic acid, the LE probes have a segment that hybridizes with a preamplifier (PA) probe of a nucleic acid multimer. The function of the PA probe is to form the first prong of the signal amplification network, which also includes amplifier probes and labeled oligonucleotides that hybridize to the amplifier probes (FIGS. 1 and 2). In some embodiments each PA probe hybridizes with two different LE probes as shown in FIGS. 1 and 2. The motif formed by the two LE probes is called a cruciform and has been shown to improve the sensitivity of binding to target nucleic acids. In some embodiments a PA probe may hybridize with a single LE probe.

The segments of the CE and LE probes that are complementary to the target nucleic acid sequence will typically be at least 15 nucleotides (nt) in length, usually at least 25 nt, e.g., 30 nt. In some embodiments the segments are not more than 100 nt. They will normally be chosen to bind to different sequences of the target nucleic acid. In general, they may be selected based on a variety of considerations. For example, depending upon the nature of the target nucleic acid and/or the goal of the assay, one may be interested in a consensus sequence, a sequence associated with polymorphisms, a particular phenotype or genotype, a particular strain, or the like. In order to ensure that the assay only recognizes target nucleic acids, the segments of the CE and LE probes that are complementary to the target nucleic acid may be selected so that the combination of sequences is unique to the target nucleic acids.

The segments of the CE and LE probes that are complementary, respectively, to the solid phase capture probe and the preamplifier probe of the nucleic acid multimer, are typically selected so as to avoid sequences that might be found in the target nucleic acid or other nucleic acids in a sample. This second segment may be contiguous to the first or be spaced therefrom by an intermediate non-complementary sequence. The probes may include other non-complementary sequences if desired. Preferably, these non-complementary sequences do not hinder hybridization of the complementary segments or cause non-specific binding to occur.

It will be appreciated that the complementary segments need not have perfect complementarity in order to hybridize. In many situations, hybridization will occur where no more than 10% of the bases are mismatches, ignoring loops of five or more nucleotides. Accordingly, as used herein the term "complementary" intends a degree of complementarity sufficient to provide hybridization under the hybridization conditions of the assay.

The probes used in the assay may be prepared by oligonucleotide synthesis procedures or by cloning, using standard methods known in the art. In some embodiments, the probes used in the assay may be DNA, RNA, or combinations thereof. In some embodiments the probes may include one or more modified nucleotides.

In some embodiments, the first stage of an assay comprises contacting the target nucleic acid under hybridizing conditions with the CE and LE probes. The ratio of each of the CE probes and LE probes in the hybridization buffer as compared to the anticipated moles of target nucleic acid is at least stoichiometric and preferably in excess. Hybridization can be carried out at a mildly elevated temperature, generally in the range from 20 to 80° C., 30 to 80° C., 35 to 75° C., 40 to 70° C., 50 to 70° C., 55 to 70° C., 60 to 70° C., particularly 65° C.

In some embodiments, after hybridization of the CE and LE probes to the target nucleic acid for a period of time, the product is contacted under hybridizing conditions with the solid phase. During this step in the assay, the CE probes hybridize to the solid phase capture probes that are bound to the solid phase. In some embodiments, the solid phase may be present when the CE and LE probes are mixed with the target nucleic acid.

Following hybridization of the CE probe-target nucleic acid-LE probe complex with the solid phase capture probes, the solid phase is washed to remove any unbound material. Next, detection of the captured target nucleic acid is achieved using one or more available detection methods.

Target Nucleic Acid Detection

In some embodiments, the captured target nucleic acid is detected using a nucleic acid multimer that includes a preamplifier (PA) probe and a multiplicity of amplifier probes (e.g., as shown in FIG. 1 or 2). The PA probe includes a segment that has a sequence, length, and composition that permits it to bind specifically to the segment of the LE probes that is not complementary to the target nucleic acid. In some embodiments, in order to achieve such specificity, this PA probe segment is 15 to 50, preferably 15 to 30, nucleotides (nt) in length and has a GC content in the range of 40% to 60%. The amplifier probes are in turn designed so that they are capable of hybridizing specifically and stably to a labeled oligonucleotide. In some embodiments, the amplifier probes may be 15 to 50, preferably 15 to 30, nucleotides (nt) in length and have a GC content in the range of 40% to 60%. In some embodiments a nucleic acid multimer may be designed to hybridize to another nucleic acid multimer.

It is to be understood that the probes of the multimer may be composed of RNA, DNA, or combinations thereof. It is also to be understood that the probes of the multimer may include modified nucleotides.

Non-Covalent Multimers

In some embodiments, nucleic acid multimers are created using a non-covalent scaffold (e.g., see FIG. 1). In the non-covalent multimer scaffold, PA probes are added to the solid-phase bound target nucleic acid-probe complex under hybridization conditions. Under these conditions, the PA probes hybridize to the available segments of the LE probes (FIG. 1). The resulting solid phase complex with the bound PA probes may be separated from any unbound PA probe by washing.

After PA probe hybridization to the solid-phase bound target nucleic acid, amplifier probes are added. These amplifier probes have a region in their sequence that is complementary to a segment of the PA probe. As a result of the design of the sequences in both the PA probes and the amplifier probes, multiple amplifier probes can anneal to a single PA probe (FIG. 1). After the amplifier probes are allowed to anneal to the solid-phase bound target nucleic acid via the PA probes, any unbound amplifier probes may be removed by washing.

The addition of the amplifier probes to the assay enables signal amplification during detection. Indeed, the multiple amplifier probes each serve as a template for the labeled oligonucleotides that are used to detect the presence of the captured target nucleic acid.

Covalent Multimers

In some embodiments, nucleic acid multimers have a covalent scaffold (e.g., see FIG. 2). In such embodiments, the PA probe and amplifier probes may be covalently linked to each other through phosphodiester bonds or through interposed linking agents such as nucleic acid, amino acid, carbohydrate or polyol bridges, or through other cross-linking agents that are capable of cross-linking nucleic acid or modified nucleic acid strands. The site(s) of linkage may be at the ends of the unit (in either normal 3'-5' orientation or randomly oriented) and/or at one or more internal nucleotides in the strand. FIG. 2 shows one type of covalent nucleic acid multimer which has a PA probe backbone with a multiplicity of pendant amplifier probes (a "comb" architecture). The pendant amplifier probes will normally depend from a modified nucleotide or other organic moiety of the PA probe having appropriate functional groups to which the amplifier probes may be conjugated or otherwise attached. In some embodiments a linear multimer may be used wherein individual amplifier probes are linked end-to-end from the preamplifier probe to form a linear polymer. In one type of covalent nucleic acid multimer two or more PA probes emanate from a point of origin to form a branched structure (a "fork" architecture). The point of origin may be another oligonucleotide unit or a multifunctional molecule to which at least three probes can be covalently bound. In general, a multimer may be totally linear, totally branched, or have a combination of linear and branched portions.

Synthesis of Multimers

The multimers may be prepared by cloning (if linear), enzymatic assembly, chemical cross-linking techniques, direct chemical synthesis or a combination thereof. In the case of linear multimers prepared by cloning, nucleic acid sequences that encode the entire multimer or fragments thereof can be made in single- or double-stranded form by conventional cloning procedures. When made in double-stranded form, the multimers/fragments are ultimately denatured to provide single-stranded multimers/fragments. Multimers may be cloned in single-stranded form using conventional single-stranded phage vectors such as M13. Fragments can be linked enzymatically or chemically to form the multimer. When assembled enzymatically, the individual units may be ligated with a ligase such as T4 DNA or RNA ligase. When prepared by chemical cross-linking, the individual units may be synthesized with one or more nucleic acids that have been derivatized to have functional groups that provide linking sites or derivatized after the oligonucleotide has been synthesized to provide such sites. In some embodiments, chemical cross-linking is achieved by incorporating $N^4$-modified cytosine bases into the nucleotide as described in U.S. Pat. No. 5,093,232. When prepared by direct chemical synthesis, oligonucleotides containing derivatized nucleic acids or equivalent multifunctional molecules whose functional groups are blocked may be made by conventional oligonucleotide synthesis techniques. The functional groups are unblocked and oligonucleotide units are synthesized out from the unblocked site(s). Generic structures for the molecules used to generate branch points in the multimers and the general methods of making these molecules are described in U.S. Pat. Nos. 5,124,246, 5,635,352 and 5,681,697 and references cited therein.

Labeled Oligonucleotides

Once the nucleic acid multimers are bound to the target nucleic acid via the LE probes, unbound nucleic acid multimers may be washed away. Labeled oligonucleotides with sequence complementary to the amplifier probes are then added to the assay. These labeled oligonucleotides become bound to the nucleic acid multimers via hybridization to the amplifier probes (e.g., see FIGS. 1 and 2).

The labeled oligonucleotides are complementary to a sequence in an amplifier probe and are functionalized with one or more labels, which directly or indirectly provide for a detectable signal. The labels may be bound to individual members of the complementary sequence or may be present as a terminal member or terminal tail having a plurality of labels. Various means for providing labels have been reported in the literature. See, for example, Leary et al., Proc Natl Acad Sci USA (1983) 80:4045; Renz and Kurz, Nucl Acids Res (1984) 12:3435; Richardson and Gumport, Nucl Acids Res (1983) 11:6167; Smith et al., Nucl Acids Res (1985) 13:2399; Meinkoth and Wahl, Anal Biochem (1984) 138:267. Labels may be bound either covalently or non-covalently. Labels which may be employed include radionuclides, fluorescers, chemiluminescers, dyes, enzymes, enzyme substrates, enzyme cofactors, enzyme inhibitors, enzyme subunits, metal ions, and the like. Examples of specific labels include but are not limited to, fluorescein, rhodamine, Texas red, phycoerythrin, umbelliferone, luminol, NADPH, $\alpha,\beta$-galactosidase, and horseradish peroxidase.

The labeled oligonucleotides are added under conditions which permit hybridization of the labeled oligonucleotide to the complementary sequence of the amplifier probes. The resulting solid phase labeled nucleic acid complex is then separated from excess labeled oligonucleotide by washing to remove unbound labeled oligonucleotide.

It will be appreciated that the procedure used in this and any of the previous separation steps of the assay will vary depending upon the nature of the solid phase. For particles, centrifugation, magnetic forces or filtration may provide for separation of the particles, discarding the supernatant or isolating the supernatant. Where the particles are assayed, the particles may be washed thoroughly, e.g., from one to five times, with an appropriate buffered medium, e.g., PBS containing a detergent—such as SDS. When the solid phase is a wall or support, the supernatant may be isolated or discarded and the wall washed in the same manner as indicated for the particles.

In certain embodiments, once the unbound labeled oligonucleotides have been removed by washing, the signal from the bound labeled oligonucleotides detected using an appropriate detection method. The detection method used to identify the presence of the target nucleic acid in the assay will depend on the nature of the labeled oligonucleotide. For example, in embodiments where the labeled oligonucleotide is functionalized with a fluorophore, the fluorescence of the fluorophore may be detected using various detection methods available in the art. For oligonucleotides labeled with chemiluminescers, luminometers or films are available for analyte detection. With enzymes, a fluorescent, chemiluminiscent, or colored product can be provided and determined fluorometrically, luminometrically, spectrophotometrically or visually. It is to be understood that any of the various labels which have been employed in immunoassays and the techniques applicable to immunoassays can be employed with the subject assays. In some embodiments, the signal is quantified using the appropriate detection method and used to calculate an amount of target nucleic acid present in the original sample.

Since the nucleic acid multimers include a relatively large number of amplifier probes that are available for binding of the labeled oligonucleotide, many more label groups become bound to the complex than there are multimers bound to the target nucleic acid. The large number of label groups decreases the threshold level of detectable target nucleic acid.

Additionally, the amplification may be multiplied by the use of more than one multimer in the assay. In such instances a first multimer is designed to function as or to bind to the amplifier probe and to a second multimer and the second multimer is designed to bind to the first multimer and to the labeled oligonucleotide. Any number of multimers may be bound in series in this manner to achieve even greater signal amplification.

The labeled oligonucleotides can be conveniently prepared by chemical synthesis such as that described in U.S. Pat. No. 5,093,232. By providing for a terminal group which has a convenient functionality, various labels may be joined through the functionality. Thus, one can provide for a carboxy, thiol, amine, hydrazine or other functionality to which the various labels may be joined without detrimentally affecting duplex formation with the amplifier probes. As previously discussed, one can have an oligonucleotide with one or more directly detectable labels. Alternatively, one can have an oligonucleotide with one or more ligands and use a labeled receptor for binding to the ligand to provide the labeled analyte complex.

Sulfonic Acid Polymer Additives

The time-limiting step of the assay is the series of hybridization reactions that occur between the LE probes and the target nucleic acid, between the target nucleic acid and the CE probes, and between the CE probes and the capture probes bound to the solid phase. In one aspect, methods are provided in which the hybridization process is accelerated by contacting the target nucleic acid under hybridizing conditions with the LE and CE probes in the presence of a sulfonic acid polymer or a salt thereof.

As demonstrated in the examples, we found that polyvinylsulfonic acid and to a lesser extent polyantholesulfonic acid performed the best in the assay. Thus, in some embodiments, the sulfonic acid polymer or salt thereof is related to polyvinylsulfonic acid and is of general formula (I):

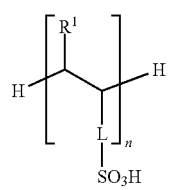

(I)

or a salt thereof, wherein:
$R^1$ is hydrogen or $C_{1-6}$ aliphatic;
L is a covalent bond or $C_{1-6}$ alkylene; and
n is an integer greater than 10.

In some embodiments, $R^1$ is hydrogen. In some embodiments, $R^1$ is $C_{1-6}$ aliphatic.

In some embodiments, L is a covalent bond. In some embodiments, L is $C_{1-6}$ alkylene. In some embodiments, L is methylene.

In some embodiments, the sulfonic acid polymer or salt thereof is of general formula (Ia):

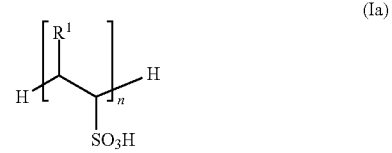

(Ia)

or a salt thereof, wherein:
$R^1$ is hydrogen or $C_{1-6}$ aliphatic.

In some embodiments, the sulfonic acid polymer or salt thereof is polyvinylsulfonic acid or a salt thereof.

In some embodiments, the sulfonic acid polymer or salt thereof is related to polyantholesulfonic acid and is of general formula (II):

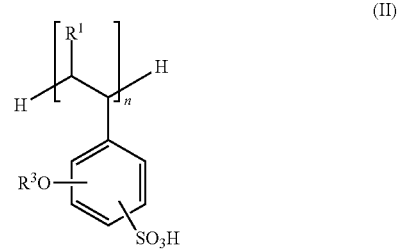

(II)

or a salt thereof, wherein:
$R^1$ is hydrogen or $C_{1-6}$ aliphatic;
$R^3$ is hydrogen or $C_{1-6}$ alkyl; and
n is an integer greater than 10.

In some embodiments, the sulfonic acid polymer or salt thereof is of general formula (IIa):

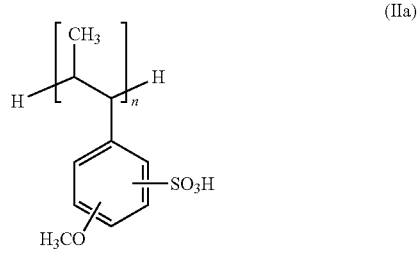

(IIa)

or a salt thereof.

In some embodiments, the sulfonic acid polymer or salt thereof is polyantholesulfonic acid or a salt thereof.

In any one of the aforementioned embodiments, n may be an integer from 10 to 200, from 10 to 150, from 10 to 100, from 10 to 90, from 10 to 80, from 10 to 70, from 20 to 150, from 30 to 150, from 40 to 150, from 50 to 150, from 60 to 150, from 70 to 150, from 80 to 150, from 90 to 150, from 100 to 150, from 50 to 120, from 60 to 120, from 70 to 120, from 80 to 120, from 90 to 120, etc.

In any one of the aforementioned embodiments, the sulfonic acid polymer or salt thereof may have an average molecular weight in the range from 500 to 1,000 Da, 1,000 to 2,000 Da, 2,000 to 4,000 Da, 3,000 to 5,000 Da, 4,000 to 6,000 Da, 5,000 to 7,000 Da, 6,000 to 8,000 Da, 7,000 to 9,000 Da, 8,000 to 10,000 Da, 2,000 to 10,000 Da, 3,000 to 10,000 Da, 4,000 to 10,000 Da, 5,000 to 10,000 Da, 6,000 to 10,000 Da, 7,000 to 10,000 Da, 2,000 to 9,000 Da, 3,000 to 9,000 Da, 4,000 to 9,000 Da, 5,000 to 9,000 Da, 6,000 to 9,000 Da, 7,000 to 9,000 Da, or 8,000 to 9,000 Da. In some embodiments, the average molecular weight is less than 1,000 Da, less than 2,000 Da, less than 3,000 Da, less than 4,000 Da, less than 5,000 Da, less than 6,000 Da, less than 7,000 Da, less than 8,000 Da, less than 9,000 Da or less than 10,000 Da.

As demonstrated in the examples, we also found that sulfonic acid polymers of lower molecular weight performed better than other higher molecular anionic polymers. Thus, in some embodiments, the sulfonic acid polymer or salt thereof is of general formula (III):

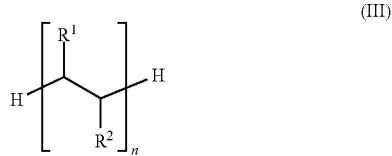

wherein:
$R^1$ is hydrogen or $C_{1-6}$ aliphatic;
$R^2$ is a covalent bond, $C_{1-6}$ aliphatic, phenyl, or a 6-membered heteroaryl ring having 1-3 nitrogens, wherein:
  $R^2$ is substituted with 1 or 2-$SO_3H$ groups or a salt thereof, provided that when $R^2$ is a covalent bond, only 1-$SO_3H$ group or a salt thereof is present, and
  $R^2$ is optionally substituted with 1-2 groups independently selected from —$R^3$, halogen, —CN, —$NO_2$, —$OR^3$, —$N(R^3)_2$, and —$SR^3$, wherein each $R^3$ is independently hydrogen or a $C_{1-6}$ alkyl group; and
n is such that the sulfonic acid polymer or salt thereof has an average molecular weight of less than 10,000 Da.

In some embodiments, the sulfonic acid polymer or salt thereof of formula (III) has an average molecular weight in the range from 500 to 1,000 Da, 1,000 to 2,000 Da, 2,000 to 4,000 Da, 3,000 to 5,000 Da, 4,000 to 6,000 Da, 5,000 to 7,000 Da, 6,000 to 8,000 Da, 7,000 to 9,000 Da, 8,000 to 10,000 Da, 2,000 to 10,000 Da, 3,000 to 10,000 Da, 4,000 to 10,000 Da, 5,000 to 10,000 Da, 6,000 to 10,000 Da, 7,000 to 10,000 Da, 2,000 to 9,000 Da, 3,000 to 9,000 Da, 4,000 to 9,000 Da, 5,000 to 9,000 Da, 6,000 to 9,000 Da, 7,000 to 9,000 Da, or 8,000 to 9,000 Da. In some embodiments, the average molecular weight is less than 1,000 Da, less than 2,000 Da, less than 3,000 Da, less than 4,000 Da, less than 5,000 Da, less than 6,000 Da, less than 7,000 Da, less than 8,000 Da, less than 9,000 Da or less than 10,000 Da.

In some embodiments, n in general formula (III) may be an integer from 10 to 200, from 10 to 150, from 10 to 100, from 10 to 90, from 10 to 80, from 10 to 70, from 20 to 150, from 30 to 150, from 40 to 150, from 50 to 150, from 60 to 150, from 70 to 150, from 80 to 150, from 90 to 150, from 100 to 150, from 50 to 120, from 60 to 120, from 70 to 120, from 80 to 120, from 90 to 120, etc.

As discussed in the examples, we have found that the concentration of the sulfonic acid polymer in the hybridization buffer can impact the hybridization rate of the nucleic acids in the assay. In some embodiments, the concentration of the polymer in the hybridization buffer is between 0.1 and 20%, between 0.2 and 15%, between 0.2 and 10%, between 0.2 and 9%, between 0.2 and 8%, between 0.2 and 7%, between 0.2 and 6%, between 0.2 and 6%, between 0.5 and 5%, between 1 and 5%, between 1 and 4%, between 0.5 and 4%, between 0.5 and 3%, or between 1 and 2.5% weight by volume.

Hybridization Conditions

In another aspect, the present disclosure provides modified hybridization conditions (decreased hybridization volume, increased salt concentration, and/or increased probe concentrations) that provide increased hybridization reaction rates between nucleic acids in the assays. In general, it is to be understood that any one of these modified hybridization conditions can be combined in order to achieve a reduction in the hybridization time of the assay (e.g., increased salt concentration and increased probe concentration, increased salt concentration and reduced hybridization volume, increased probe concentration and reduced hybridization volume, or increased salt concentration, increased probe concentration and reduced hybridization volume). In general, it is also to be understood that any one of the previous sulfonic acid polymers can be combined with any of these modified hybridization conditions in order to achieve a reduction in the hybridization time of the assay.

In some embodiments, the modified hybridization conditions are used for the steps of the assay that involve (a) hybridization of the CE and LE probes to the target nucleic acid and (b) hybridization of the CE probes (as part of the CE probe-target nucleic acid-LE probe complex) to the solid phase capture probes. In some embodiments, the modified hybridization conditions are used for other steps of the assay, e.g., the detection steps.

Salt Concentration

When the LE and CE probes are contacted with the target nucleic acid in the presence of a sulfonic acid polymer of the present disclosure then a wide range of salt concentrations may be employed. For example, in some embodiments, the hybridizing conditions may comprise a salt concentration in the range of 100 mM to 2 M, 100 mM to 1.5 M, 100 mM to 1M, 100 mM to 750 mM, etc.

As discussed in the examples, we have also found that even in the absence of a sulfonic acid polymer, the incubation time can be significantly shortened by increasing the salt concentration (optionally combined with an increase in probe concentration and/or a decrease in the hybridization volume as described herein). Thus in some embodiments where a sulfonic acid polymer may or may not be present, the hybridizing conditions may comprise a salt concentration in the range of 350 mM to 2 M, 350 mM to 1.5 M, 350 mM to 1M, 350 mM to 750 mM, 350 mM to 650 mM, 450 mM to 2 M, 450 mM to 1.5 M, 450 mM to 1M, 450 mM to 750 mM, 450 mM to 650 mM, 550 mM to 2 M, 550 mM to 1.5 M, 550 mM to 1M, 550 mM to 750 mM, 550 mM to 650 mM, etc.

In some embodiments, the salt used in the assay is selected from the group of LiCl, NaCl, KCl, or $CaCl_2$. In some embodiments, the salt is LiCl. In some embodiments, the salt concentrations is in the range of 500 to 700 mM.

Probe Concentrations

When the LE and CE probes are contacted with the target nucleic acid in the presence of a sulfonic acid polymer of the present disclosure then a wide range of probe concentrations may be employed. For example, in some embodiments, the LE and/or CE probe concentrations may independently range from 0.1 nM to 100 nM, 0.3 nM to 100 nM, 0.5 nM to 100 nM, 0.7 nM to 100 nM, 1 nM to 100 nM, 1.5 nM to 100 nM, 2 nM to 100 nM, 5 nM to 100 nM, 10 nM to 100 nM, 25 nM to 100 nM, 50 nM to 100 nM, 0.1 nM to 10 nM, 0.3 nM to 10 nM, 0.5 nM to 10 nM, 0.7 nM to 10 nM, 1 nM to 10 nM, 1.5 nM to 10 nM, 2 nM to 10 nM, 5 nM to 10 nM, 0.1 nM to 5 nM, 0.3 nM to 5 nM, 0.5 nM to 5 nM, 0.7 nM to 5 nM, 1 nM to 5 nM, 1.5 nM to 5 nM, 2 nM to 5 nM, etc.

As discussed in the examples, we have also found that even in the absence of a sulfonic acid polymer, the incubation time can be significantly shortened by increasing the probe concentration (optionally combined with an increase in salt concentration and/or a decrease in the hybridization volume as described herein). Thus in some embodiments where a sulfonic acid polymer may or may not be present, the hybridizing conditions may comprise an LE and/or CE probe concentration in the range of 1 nM to 100 nM, 1.3 nM to 100 nM, 1.5 nM to 100 nM, 1.7 nM to 100 nM, 2 nM to 100 nM, 2.5 nM to 100 nM, 3 nM to 100 nM, 5 nM to 100 nM, 10 nM to 100 nM, 25 nM to 100 nM, 50 nM to 100 nM, 1 nM to 50 nM, 1.3 nM to 50 nM, 1.5 nM to 50 nM, 1.7 nM to 50 nM, 2 nM to 50 nM, 2.5 nM to 50 nM, 3 nM to 50 nM, 5 nM to 50 nM, 10 nM to 50 nM, 25 nM to 50 nM, 1 nM to 25 nM, 1.3 nM to 25 nM, 1.5 nM to 25 nM, 1.7 nM to 25 nM, 2 nM to 25 nM, 2.5 nM to 25 nM, 3 nM to 25 nM, 5 nM to 25 nM, 10 nM to 25 nM, 25 nM to 25 nM, 1 nM to 10 nM, 1.3 nM to 10 nM, 1.5 nM to 10 nM, 1.7 nM to 10 nM, 2 nM to 10 nM, 2.5 nM to 10 nM, 3 nM to 10 nM, 5 nM to 10 nM, 1 nM to 5 nM, 1.3 nM to 5 nM, 1.5 nM to 5 nM, 1.7 nM to 5 nM, 2 nM to 5 nM, 2.5 nM to 5 nM, 3 nM to 5 nM, etc.

In some embodiments, the concentrations of the CE and LE probes are different. In some embodiments, the concentrations of the CE and LE probes are the same. In some embodiments, the CE and/or LE probe concentrations are in the range of 1.5 to 2.5 nM.

Volume

When the LE and CE probes are contacted with the target nucleic acid in the presence of a sulfonic acid polymer of the present disclosure then a wide range of hybridization volumes (i.e., the volume of solution employed) may be employed. For example, in some embodiments, the hybridizing conditions may comprise a hybridization volume in the range of 10 uL to 1000 uL, 20 uL to 1000 uL, 30 uL to 1000 uL, 40 uL to 1000 uL, 50 uL to 1000 uL, 60 uL to 1000 uL, 70 uL to 1000 uL, 80 uL to 1000 uL, 90 uL to 1000 uL, 100 uL to 1000 uL, 250 uL to 1000 uL, 500 uL to 1000 uL, 750 uL to 1000 uL, 10 uL to 250 uL, 20 uL to 250 uL, 30 uL to 250 uL, 40 uL to 250 uL, 50 uL to 250 uL, 60 uL to 250 uL, 70 uL to 250 uL, 80 uL to 250 uL, 90 uL to 250 uL, 100 uL to 250 uL, 500 uL to 1000 uL, 750 uL to 1000 uL, etc.

As discussed in the examples, we have also found that even in the absence of a sulfonic acid polymer, the incubation time can be significantly shortened by decreasing the hybridization volume (optionally combined with an increase in salt concentration and/or an increase in probe concentration as described herein). Thus in some embodiments where a sulfonic acid polymer may or may not be present, the hybridizing conditions may comprise a hybridization volume of less than 100 uL, 95 ul, 90 uL, 85, uL, 80 uL, 75 uL, 70 uL, 65 uL, 60 uL, 55 uL, 50 uL, 45 uL, 40 uL, 35 uL, 30 uL, 25 uL, 20 uL or 10 uL. In some of these embodiments, the hybridization volume is at least 80 uL, 70 uL, 60 uL, 50 uL, 40 uL, 30 uL, 20 uL or 10 uL. In some embodiments, the hybridization volume is in the range of 10 to 100 uL, 20 to 100 uL, 30 to 100 uL, 40 to 100 uL, 50 to 100 uL, 60 to 100 uL, 70 to 100 uL, 80 to 100 uL, 90 to 100 uL, 10 to 90 uL, 20 to 90 uL, 30 to 90 uL, 40 to 90 uL, 50 to 90 uL, 60 to 90 uL, 70 to 90 uL, 80 to 90 uL, 10 to 50 uL, 20 to 50 uL, 30 to 50 uL, 40 to 50 uL, etc. In some embodiments, the hybridization volume is in the range of 40 to 60 uL.

Combinations

As mentioned above, it is to be understood that the present disclosure encompasses each and every combination of the range of variables that are discussed above. Thus any one of the disclosed salt concentration ranges may be combined with any one of the probe concentration ranges. Similarly, any one of the salt concentration ranges may be combined with any one of the hybridization volume ranges; any one of the probe concentration ranges may be combined with any one of the hybridization volume ranges. Finally, any one of the salt concentration ranges, probe concentration ranges and hybridization volume ranges may be combined.

By way of example and without limitation, the present disclosure encompasses combinations such as:

(1) a salt concentration in the range of 500 to 700 mM combined with CE and/or LE probe concentrations in the range of 1.5 to 2.5 nM;

(2) a salt concentration in the range of 500 to 700 mM combined with a hybridization volume is in the range of 40 to 60 uL;

(3) CE and/or LE probe concentrations in the range of 1.5 to 2.5 nM combined with a hybridization volume is in the range of 40 to 60 uL; and (4) a salt concentration in the range of 500 to 700 mM combined with CE and/or LE probe concentrations in the range of 1.5 to 2.5 nM and a hybridization volume in the range of 40 to 60 uL.

It is also to be understood that these combined conditions may be used in combination with any of the sulfonic acid polymers of the present disclosure (or a salt thereof).

EXAMPLES

Example 1

This example describes experiments we performed in order to investigate the influence of different components used in the target nucleic acid capture step of a Siemens HIV bDNA RNA 3.0 assay. In order to examine the effect of diffusion on the rate of hybridization we performed experiments in which the standard reaction volume was halved (from 100 ul to 50 ul). In order to examine the effect of probe concentration we performed experiments in which the standard concentrations of the label extender (LE) probes (1.2 nM) and capture extender (CE) probes (0.9 nM) were each doubled. Finally, in order to investigate the effect of components in the working hybridization buffer (i.e., salt, buffer, detergent, etc.) we doubled their concentrations from their standard values (salt: 317 mM LiCl, buffer: 21 mM HEPES sodium salt, 21 mM HEPES free acid, detergent: 4.23% lauryl sulfate lithium salt and other: 7.6 mM EDTA and 0.169% casein).

The first condition tested was the control condition, comprising 100 uL of the standard working hybridization buffer (WHB) supplemented with standard concentrations of LE and CE probes (1×WHB/1× probes (100 uL) in Table 1 below). The control reaction was compared to a hybridization reaction with half of the reaction volume (50 uL) and a two-fold increase in the LE and CE probe concentrations (1×WHB/2× probes (50 uL) in Table 1). Additionally, the rate of hybridization was investigated under conditions where the concentration of the working hybridization buffer components in the 50 uL reaction were doubled (2×WHB/2× probes (50 uL) in Table 1). The extent of nucleotide hybridization in each assay was measured using raw light unit (RLU) signal after only 1.5 hours of incubation time.

TABLE 1

| | HIV bDNA Assay 265,530 copies/mL (n = 5) | | Negative Control (n = 2) | |
|---|---|---|---|---|
| | RLU Average | % Increase | RLU Average | % Increase |
| 1× WHB/1× probes (100 uL) | 591.2 | Reference | 0.58 | Reference |
| 1× WHB/2× probes (50 uL) | 677.8 | 14.6 | 0.46 | −21 |
| 2× WHB/2× probes (50 uL) | 1477.8 | 150.0 | 0.46 | −20 |

As shown in Table 1, a ~15% increase in the raw light unit (RLU) signal was observed when the reaction volume reduced to 50 uL and the concentrations of the LE and CE probes were increased two-fold as compared to the control condition (i.e., 1×WHB/2× probes (50 uL) vs. 1×WHB/1× probes (100 uL)). Additionally, a two-fold increase in the concentration of the WHB components resulted in a ~150% increase in RLU signal as compared to the control hybridization reaction (i.e., 2×WHB/2× probes (50 uL) vs. 1×WHB/1× probes (100 uL)). These results suggest that decreasing the volume of the hybridization reaction, coupled with a two-fold increase in the concentrations of the LE and CE probes and/or an increase in the concentration of the WHB components increases the rate of hybridization in the assay.

Example 2

In this example we investigated how the hybridization rate of the preferred hybridization condition from Example 1 (i.e., 2×WHB/2× probes (50 uL)) compared to the standard reaction conditions. Three experiments were performed and changes in the nucleotide hybridization rate were quantified by the amount of raw light unit (RLU) signal measured at a particular time point.

The RLU signal was first measured for the standard conditions at three and sixteen hour time points (1×WHB/1× probes (100 uL)—3 hour, and 1×WHB/1× probes (100 uL)—16 hour, respectively in Table 2 below). Next, the RLU signal was measured for the preferred hybridization conditions from Example 1 at a three hour time point (2×WHB/2× probes (50 uL)—3 hour in Table 2).

TABLE 2

| | HIV bDNA Assay 250,000 copies/mL (n = 10) | | Negative Control (n = 6) | |
|---|---|---|---|---|
| | RLU Average | % Increase | RLU Average | % Increase |
| 1× WHB/1× probes (100 uL) - 3 hour | 1099 | Reference | 0.7 | Reference |
| 1× WHB/1× probes (100 uL) - 16 hour | 2234 | 103 | 0.5 | −31 |
| 2× WHB/2× probes (50 uL) - 3 hour | 2199 | 100 | 0.6 | −7 |

As shown in Table 2, the RLU signal for the standard condition after a sixteen hour incubation (i.e., overnight) was twice that of the RLU signal at the three hour time point. Interestingly, the preferred hybridization conditions from Example 1 (2×WHB/2× probes (50 uL)) led to about the same RLU signal after only a three hour incubation (see Table 2). These data suggest that the equilibrium reached under the standard hybridization conditions after sixteen hours can be reached in just three hours using the preferred hybridization conditions from Example 1. These results suggest that the two-fold increase in the LE and CE probe concentration coupled with a two-fold reduction in the reaction volume, and a two-fold increase in the concentration of the components of the working hybridization buffer (WHB) can be used to dramatically shorten the incubation time needed for this assay.

Example 3

In order to determine how the different components of the 2× working hybridization buffer (WHB) affected hybridization in the assay we compared two hybridization conditions. In the first, we used the preferred hybridization conditions from Example 1 (2×WHB/2× probes (50 uL) in Table 3 below). In the second, we reduced the salt concentration in the 2×WHB by half (i.e., we used the standard salt concentration, 2×WHB with 1× salt/2× probes (50 uL) in Table 3). In the reduced salt condition, the only component of the 2×WHB that was reduced from 2× to 1× was the salt (i.e., LiCl). The amount of nucleotide hybridization under the two conditions was quantified after three hours using the raw light unit (RLU) signal. The experiments were repeated with two different levels of target nucleic acid (75,000 copies/mL and 1,000 copies/mL).

TABLE 3

| | HIV bDNA Assay 75,000 copies/ mL (n = 5) | | HIV bDNA Assay 1,000 copies/mL (n = 5) | |
|---|---|---|---|---|
| | RLU Average | % Decrease | RLU Average | % Decrease |
| 2× WHB/2× probes (50 uL) | 609.7 | Reference | 9.0 | Reference |
| 2× WHB w/1× salt/2× probes (50 uL) | 310.0 | 49.2 | 7.9 | 12.3 |

As shown in Table 3, when the salt concentration was halved there was a ~12% and a ~49% decrease in RLU when 1,000 and 75,000 copies/mL of target nucleic acid were tested, respectively. These results suggest that changes in salt concentration in the working hybridization buffer have a significant impact on hybridization rate.

Example 4

In addition to investigating the effect of volume, probe concentration and the concentrations of WHB components we also investigated the impact of adding certain anionic polymers to the lysis diluent which is used to prepare the target nucleic acid sample. Traditionally, the lysis diluent used in the Siemens HIV bDNA RNA 3.0 assay contains less than 1% w/v of an uncharged hydrocarbon polymer, hetastarch (also known as Hespan), which functions as a volume exclusion agent. Volume exclusion agents have been reported to increase the rate of nucleic acid hybridization (e.g., see U.S. Pat. Nos. 4,302,204 and 5,853,986). In our experiments we replaced hetastarch in the lysis diluent with different anionic polymers and measured the raw light unit (RLU) signal after a three hour incubation period (standard WHB and LE/CE probe concentrations were used). Anionic polymers tested in the lysis diluent included 1% w/v of polyvinylsulfonic acid (Sigma #278424-5ML, average molecular weight of 3,000 to 10,000 Da), 1% w/v of polyantholesulfonic acid (Sigma #444464-5G, average molecular weight of 9,000 to 11,000 Da), and 1% w/v of a higher molecular weight polyacrylic acid (Sigma #523925-100ML, average molecular weight of 100,000 Da). The experiments were repeated with two different levels of target nucleic acid (75,000 copies/mL and 10,000 copies/mL). CV is a statistical measure of variance from the RLU average.

TABLE 4

| | HIV bDNA Assay 75,000 copies/mL (n = 5) | | | HIV bDNA Assay 10,000 copies/mL (n = 6) | | |
|---|---|---|---|---|---|---|
| | RLU Average | CV | % Increase | RLU Average | CV | % Increase |
| Lysis Diluent with Hetastarch | 592.14 | 8.03 | Reference | 84.0 | 6.18 | Reference |
| 1% Polyvinylsulfonic Acid | 855.60 | 9.42 | 44.5 | 111.1 | 10.75 | 32.2 |
| 1% Polyantholesulfonic Acid | 752.90 | 4.59 | 27.1 | 94.1 | 5.24 | 12.1 |
| 1% Polyacrylic Acid | 620.18 | 7.66 | 4.7 | 79.5 | 11.44 | −5.4 |

Replacing hetastarch with the low molecular weight polysulfonic acid polymers polyvinylsulfonic acid and polyantholesulfonic acid had a positive effect on the RLU signal after the three hour incubation time. Of note, replacing hetastarch with the much higher molecular weight polyacrylic acid did not have the same effect. Polyvinylsulfonic acid showed the strongest effect with a ~32-45% increase in RLU as compared to the standard lysis diluent with hetastarch.

Example 5

This example describes experiments that were performed to determine whether anionic polymers (including those of Example 4) had a positive effect on the hybridization process in the Siemens HCV 3.0 bDNA assay. Again, hetastarch in the standard lysis diluent was replaced with different anionic polymers at 1% w/v. This time we used three different polysulfonic acid polymers, namely: the polyvinylsulfonic acid and polyantholesulfonic acid of Example 4 and higher molecular weight polystyrenesulfonic acid (Sigma #561223-100G, average molecular weight of ~75,000 Da). The nucleotide hybridization in these assays was measured after three hours using the raw light unit (RLU) signal.

TABLE 5

| | HCV bDNA Assay 4,695,688 copies/mL (n = 5) | | |
|---|---|---|---|
| | RLU Average | CV | % Increase |
| Lysis Diluent with Hetastarch | 1366 | 8.0 | Reference |
| 1% Polyvinylsulfonic Acid | 1524 | 6.9 | 11.6 |

TABLE 5-continued

| | HCV bDNA Assay 4,695,688 copies/mL (n = 5) | | |
|---|---|---|---|
| | RLU Average | CV | % Increase |
| 1% Polyantholesulfonic Acid | 1473 | 6.3 | 7.9 |
| 1% Polystyrenesulfonic Acid | 1406 | 6.3 | 2.9 |

As shown in Table 4, while the sulfonic acid polymers led to an increase in signal it was somewhat reduced as compared to the HIV assay in Example 4. It was also noteworthy that the lower molecular weight polyvinylsulfonic acid and polyantholesulfonic acid outperformed the higher molecular weight polystyrenesulfonic acid. The results were also consistent with the results of Example 4, in that addition of polyvinylsulfonic acid to the lysis diluent contributed to the largest increase in RLU.

Example 6

This example describes experiments that were performed to determine whether the amount of anionic polymer used in the lysis diluent impacts the hybridization process in the Siemens HCV 3.0 bDNA assay. The lysis diluent was formulated with either polyvinylsulfonic acid or polyantholesulfonic acid at percentages of 1% or 0.5% w/v. The nucleotide hybridization was measured after three hours using the raw light unit (RLU) signal. The RLU signals were compared to those from a control assay using the standard lysis diluent with hetastarch.

TABLE 6

| | HCV bDNA Assay 4,695,688 copies/mL (n = 5) | | | HCV bDNA Assay 469,569 copies/mL (n = 6) | | |
|---|---|---|---|---|---|---|
| | RLU Average | CV | % Increase | RLU Average | CV | % Increase |
| Lysis Diluent with Hetastarch | 680.5 | 4.86 | Reference | 47.0 | 5.94 | Reference |
| 1% Polyvinylsulfonic Acid | 734.0 | 1.74 | 7.9 | 55.8 | 3.70 | 18.8 |
| 0.5% Polyvinylsulfonic Acid | 719.6 | 4.51 | 5.8 | 52.7 | 6.87 | 12.2 |
| 1% Polyantholesulfonic Acid | 717.6 | 0.81 | 5.5 | 53.2 | 3.75 | 13.4 |
| 0.5% Polyantholesulfonic Acid | 715.0 | 2.66 | 5.1 | 50.4 | 1.79 | 7.2 |

The anionic polymers at 1% or 0.5% w/v had a positive effect as measured by RLU signal. Consistent with the results of Example 4, the addition of polyvinylsulfonic acid contributed to the largest increase in RLU. In addition, the assays performed with 1% w/v of either polyvinylsulfonic acid or polyantholesulfonic acid showed a larger increase in the RLU signal as compared to the assays performed with 0.5% of the corresponding polymer.

Example 7

The previous examples have identified polyvinylsulfonic acid (PVSA) as a preferred anionic polymer for reducing incubation times. In this experiment we tested a range of PVSA concentrations (2.5, 1.0 and 0.5% w/v) using the Siemens HIV bDNA RNA 3.0 assay with a three hour incubation time. The RLU signals were compared to those from a control assay using the standard lysis diluent with hetastarch.

TABLE 7

|  | HIV bDNA Assay 75,000 copies/mL (n = 5) | | | HIV bDNA Assay 10,000 copies/mL (n = 6) | | |
|---|---|---|---|---|---|---|
|  | RLU Average | CV | % Increase | RLU Average | CV | % Increase |
| Lysis Diluent with Hetastarch | 517.76 | 17.30 | Reference | 63.19 | 10.55 | Reference |
| 2.5% Polyvinylsulfonic Acid | 751.64 | 5.75 | 45.2 | 99.27 | 6.35 | 57.1 |
| 1.0% Polyvinylsulfonic Acid | 624.04 | 11.28 | 20.5 | 92.94 | 13.28 | 47.1 |
| 0.5% Polyvinylsulfonic Acid | 576.08 | 5.76 | 11.3 | 90.34 | 9.01 | 43.0 |

The assays performed with the lysis diluent formulated with either 0.5, 1.0 and 2.5% w/v PVSA each showed an increase in RLU signal. In addition, the results of this experiment suggest that the increased rate of hybridization as measured by RLU signal is correlated with the amount of PVSA added to the lysis diluent.

Example 8

In a final series of experiments we set out to determine whether the different effects observed in the previous examples could be combined (i.e., effect of reducing volume, increasing probe concentration, increasing WHB salt concentration and adding an anionic polymer such as PVSA polymer).

We first investigated if adding 1.25% PVSA could further increase the RLU observed with the preferred hybridization condition from Example 1 (i.e., 2×WHB/2× probes (50 uL)). A two hour incubation period was tested. The standard 100 uL reaction with the 1× working hybridization buffer was used as a control (1×WHB/1× Probes (100 uL)). These conditions were tested using the Siemens HIV bDNA RNA 3.0 assay.

TABLE 8

|  | HIV bDNA Assay 75,000 copies/mL (n = 4) | | |
|---|---|---|---|
|  | RLU Average | CV | % Increase |
| 1× WHB/1× Probes (100 uL) | 4.34 | 7.24 | N/A |
| 2× WHB/2× Probes (50 uL) | 9.35 | 5.79 | Reference |
| 2× WHB, 1.25% PVSA/2× Probes (50 uL) | 11.79 | 10.03 | 25 |

As shown in Table 8, a ~25% increase in RLU signal was observed over the RLU signal from the assay using the 2×WHB/2× Probes (50 uL). This data supports that addition of an anionic polymer such as PVSA can further increase the rate of hybridization in the assay.

Tables 9, 10, 11 and 12 show results from other experiments that we performed using various incubation times. The results from these experiments are generally consistent with the results in Table 8.

TABLE 9

| (2.5 hour incubation time): | | | | | | | | | |
|---|---|---|---|---|---|---|---|---|---|
|  | HIV bDNA Assay 250,000 copies/mL (n = 5) | | | HIV bDNA Assay 75,000 copies/mL (n = 5) | | | HIV bDNA Assay 1,000 copies/mL (n = 5) | | |
|  | RLU Ave. | CV | % Inc. | RLU Ave. | CV | % Inc. | RLU Ave. | CV | % Inc. |
| 1× WHB/1× Probes (100 uL) | 1,162 | 10.8 | Ref. | 267 | 11.3 | Ref. | 4.3 | 10.9 | Ref. |
| 2× WHB/2× Probes (50 uL) | 2,180 | 16.1 | 87.6 | 720 | 10.7 | 169.7 | 8.5 | 9.4 | 96.4 |
| 2× WHB, 1.25% PVSA/2× Probes (50 uL) | 2,216 | 3.2 | 90.6 | 896 | 11.1 | 235.9 | 12.1 | 6.7 | 181.2 |

TABLE 10

(overnight incubation):

| | HIV bDNA Assay 250,000 copies/mL (n = 5) | | | HIV bDNA Assay 75,000 copies/mL (n = 5) | | | HIV bDNA Assay 1,000 copies/mL (n = 5) | | |
|---|---|---|---|---|---|---|---|---|---|
| | RLU Ave. | CV | % Inc. | RLU Ave. | CV | % Inc. | RLU Ave. | CV | % Inc. |
| 1x WHB/1x Probes (100 uL) | 3,250 | 7.0 | Ref. | 950 | 3.5 | Ref. | 13.6 | 5.6 | Ref. |
| 2x WHB/2x Probes (50 uL) | 4,007 | 3.0 | 23.3 | 1,407 | 13.9 | 48.1 | 19.4 | 9.3 | 42.5 |
| 2x WHB, 1.25% PVSA/2x Probes (50 uL) | 4,374 | 3.9 | 34.6 | 1,620 | 10.1 | 70.5 | 22.8 | 8.0 | 67.6 |

TABLE 11

(2 hour incubation time):

| | HIV bDNA Assay 250,000 copies/mL (n = 5) | | | HIV bDNA Assay 75,000 copies/mL (n = 5) | | | HIV bDNA Assay 1,000 copies/mL (n = 5) | | |
|---|---|---|---|---|---|---|---|---|---|
| | RLU Ave. | CV | % Inc. | RLU Ave. | CV | % Inc. | RLU Ave. | CV | % Inc. |
| 1x WHB/1x Probes (100 uL) | 332 | 22.4 | Ref. | 286.95 | 7.2 | Ref. | 4.3 | 8.31 | Ref. |
| 2x WHB/2x Probes (50 uL) | 1,532 | 18.0 | 362 | 658.38 | 5.8 | 129 | 9.4 | 9.18 | 116 |
| 2x WHB, 1% PVSA/2x Probes (50 uL) | 1,864 | 4.4 | 462 | 648.90 | 6.8 | 126 | 9.1 | 6.43 | 109 |
| 2x WHB, 1.25% PVSA/2x Probes (50 uL) | 1,777 | 7.3 | 436 | 820.40 | 10.0 | 186 | 12.0 | 6.08 | 172 |

TABLE 12

(3 hour incubation time):

| | HIV bDNA Assay 75,000 copies/mL (n = 5) | | | HIV bDNA Assay 1,000 copies/mL (n = 6) | | |
|---|---|---|---|---|---|---|
| | RLU Average | CV | % Inc. | RLU Average | CV | % Inc. |
| 1x WHB/1x Probes (100 uL) | 371.96 | 18.19 | Reference | 7.05 | 8.82 | Reference |
| 2x WHB/2x Probes (50 uL) | 937.88 | 10.90 | 152.1 | 12.25 | 10.24 | 73.7 |
| 2x WHB, 1% PVSA/2x Probes (50 uL) | 970.90 | 7.00 | 161.0 | 13.83 | 6.48 | 96.1 |
| 2x WHB, 2.5% PVSA/2x Probes (50 uL) | 921.82 | 10.71 | 147.8 | 13.22 | 15.98 | 87.5 |

OTHER EMBODIMENTS

Other embodiments of the invention will be apparent to those skilled in the art from a consideration of the specification or practice of the invention disclosed herein. It is intended that the specification and examples be considered as exemplary only, with the true scope and spirit of the invention being indicated by the following claims.

We claim:

1. A solution nucleic acid hybridization assay for detecting a target nucleic acid that comprises first and second nucleic acid sequences comprising:

(a) contacting a target nucleic acid under hybridizing conditions with a sulfonic acid polymer or a salt thereof and an excess, relative to the target nucleic acid, of (i) a label extender probe comprising first and second segments, wherein the first segment is complementary to a first nucleic acid sequence of the target nucleic acid and (ii) a capture extender probe comprising first and second segments, wherein the first segment is complementary to a second nucleic acid sequence of the target nucleic acid;

(b) contacting under hybridizing conditions the product of step (a) with a capture probe bound to a solid phase that is complementary to the second segment of the capture extender probe, thereby forming a solid phase complex product;

(c) removing materials not bound to the solid phase complex product;

(d) contacting under hybridizing conditions the solid phase complex product of step (c) with a nucleic acid multimer that comprises (i) a preamplifier probe that is complementary to the second segment of the label extender probe and (ii) a multiplicity of amplifier probes;

(e) removing unbound nucleic acid multimer from the solid phase complex product of step (d);

(f) contacting under hybridizing conditions the solid phase complex product of step (e) with a labeled oligonucleotide that is complementary to the multiplicity of amplifier probes of the nucleic acid multimer;

(g) removing unbound labeled oligonucleotide from the solid phase complex product of step (f); and (h) detecting the presence of labeled oligonucleotide in the solid phase complex product of step (g), wherein the sulfonic acid polymer or salt thereof in step (a) is of general formula (I) or (II):

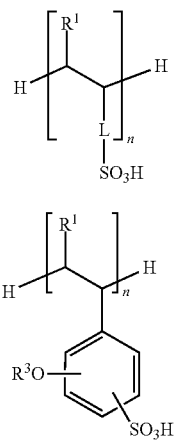

or a salt thereof, wherein:
R¹ is hydrogen or $C_{1-6}$ aliphatic;
L is a covalent bond or $C_{1-6}$alkylene;
R³ is hydrogen or $C_{1-6}$ alkyl; and
n is 10 or an integer greater than 10; and
wherein the sulfonic acid polymer or salt thereof has an average molecular weight of 9,000 Da or less.

2. The assay of claim 1, wherein the multiplicity of amplifier probes are hybridized to a first preamplifier probe of the nucleic acid multimer.

3. The assay of claim 1, wherein the multiplicity of amplifier probes are covalently linked to the preamplifier probe of the nucleic acid multimer.

4. The assay of claim 1, wherein the sulfonic acid polymer or salt thereof is of general formula (I).

5. The assay of claim 4, wherein the sulfonic acid polymer or salt thereof is of general formula (Ia):

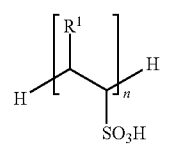

or a salt thereof.

6. The assay of claim 4, wherein the sulfonic acid polymer or salt thereof is polyvinylsulfonic acid or a salt thereof.

7. The assay of claim 1, wherein the sulfonic acid polymer or salt thereof is of general formula (II).

8. The assay of claim 7, wherein the sulfonic acid polymer or salt thereof is of general formula (IIa):

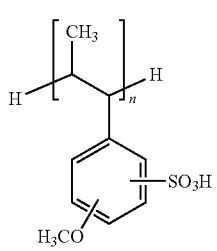

or a salt thereof.

9. The assay of claim 7, wherein the sulfonic acid polymer or salt thereof is polyanetholesulfonic acid or a salt thereof.

10. The assay of claim 1, wherein n is an integer from 10 to 200.

11. The assay of claim 1, wherein the sulfonic acid polymer or salt thereof has an average molecular weight of less than 8,000 Da.

12. The assay of claim 1, wherein the sulfonic acid polymer or salt thereof has an average molecular weight of less than 6,000 Da.

13. The assay of claim 1, wherein the sulfonic acid polymer or salt thereof has an average molecular weight of less than 4,000 Da.

14. The assay of claim 1, wherein the sulfonic acid polymer or salt thereof is present at a concentration of between 0.2 and 10% weight by volume.

15. The assay of claim 1, wherein the sulfonic acid polymer or salt thereof is present at a concentration of between 0.5 and 5% weight by volume.

16. The assay of claim 1, wherein the sulfonic acid polymer or salt thereof is present at a concentration of between 1 and 2.5% weight by volume.

17. The assay of claim 1, wherein the sulfonic acid polymer or salt thereof has an average molecular weight of less than 9,000 Da and is present at a concentration of between 0.2 and 10% weight by volume.

18. The assay of claim 1, wherein the hybridizing conditions in steps (a) and (b) comprise a salt concentration in the range of 500 to 700 mM.

19. The assay of claim 1, wherein the label extender probe andor capture extender probe concentration in step (a) is in the range of 1.5 to 2.5 nM.

20. The assay of claim 1, wherein the hybridizing conditions in steps (a) and (b) comprise a hybridization volume in the range of 40 to 60 uL.

21. The assay of claim 1, wherein the hybridizing conditions in steps (a) and (b) comprise a salt concentration in the range of 500 to 700 mM and a hybridization volume in the range of 40 to 60 uL; and the label extender probe andor capture extender probe concentration in step (a) is in the range of 1.5 to 2.5 nM.

22. The assay of claim 21, wherein the sulfonic acid polymer or salt thereof has an average molecular weight of less than 9,000 Da and is present at a concentration of between 0.2 and 10% weight by volume.

23. The assay of claim 22, wherein the sulfonic acid polymer or salt thereof is polyvinylsulfonic acid or a salt thereof.

24. The assay of claim 22, wherein the sulfonic acid polymer or salt thereof is polyanetholesulfonic acid or a salt thereof.

25. The assay of claim 1, wherein the sulfonic acid polymer or salt thereof has an average molecular weight in the range of from 1,000 to 2,000 Da.

26. The assay of claim 1, wherein the sulfonic acid polymer or salt thereof has an average molecular weight in the range of from 3,000 to 5,000 Da.

27. The assay of claim 1, wherein the sulfonic acid polymer or salt thereof has an average molecular weight in the range of from 5,000 to 7,000 Da.

28. The assay of claim 1, wherein the sulfonic acid polymer or salt thereof has an average molecular weight in the range of from 7,000 to 9,000 Da.

29. A solution nucleic acid hybridization assay for detecting a target nucleic acid that comprises first and second nucleic acid sequences comprising:
(a) contacting a target nucleic acid under hybridizing conditions with a sulfonic acid polymer or a salt thereof and an excess, relative to the target nucleic acid, of (i) a label extender probe comprising first and second segments, wherein the first segment is complementary to a first nucleic acid sequence of the target nucleic acid and (ii) a capture extender probe comprising first and second segments, wherein the first segment is complementary to a second nucleic acid sequence of the target nucleic acid;
(b) contacting under hybridizing conditions the product of step (a) with a capture probe bound to a solid phase that is complementary to the second segment of the capture extender probe, thereby forming a solid phase complex product;
(c) removing materials not bound to the solid phase complex product;
(d) contacting under hybridizing conditions the solid phase complex product of step (c) with a nucleic acid multimer that comprises (i) a preamplifier probe that is complementary to the second segment of the label extender probe and (ii) a multiplicity of amplifier probes;
(e) removing unbound nucleic acid multimer from the solid phase complex product of step (d);
(f) contacting under hybridizing conditions the solid phase complex product of step (e) with a labeled oligonucleotide that is complementary to the multiplicity of amplifier probes of the nucleic acid multimer;
(g) removing unbound labeled oligonucleotide from the solid phase complex product of step (f); and
(h) detecting the presence of labeled oligonucleotide in the solid phase complex product of step (g),
wherein the sulfonic acid polymer or salt thereof in step (a) is of general formula (III):

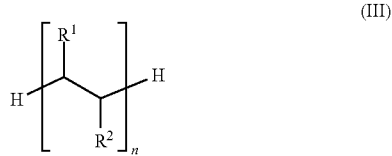

wherein:
$R^1$ is hydrogen or $C_{1-6}$ aliphatic;
$R^2$ is a covalent bond, $C_{1-6}$ aliphatic, phenyl, or a 6-membered heteroaryl ring having 1-3 nitrogens, wherein:
$R^2$ is substituted with 1 or 2 —$SO_3H$ groups or a salt thereof, provided that when $R^2$ is a covalent bond, only 1 —$SO_3H$ group or a salt thereof is present, and
$R^2$ is optionally substituted with 1-2 groups independently selected from $R^3$, halogen, —CN, —$NO_2$, —$OR^3$, —$N(R^3)_2$, and —$SR^3$, wherein each $R^3$ is independently hydrogen or a $C_{1-6}$ alkyl group; and
n is such that the sulfonic acid polymer or salt thereof has an average molecular weight of 9,000 Da or less.

30. The assay of claim 29, wherein n is an integer from 10 to 200.

31. The assay of claim 29, wherein the sulfonic acid polymer or salt thereof has an average molecular weight of less than 8,000 Da.

32. The assay of claim 29, wherein the sulfonic acid polymer or salt thereof has an average molecular weight of less than 6,000 Da.

33. The assay of claim 29, wherein the sulfonic acid polymer or salt thereof has an average molecular weight of less than 4,000 Da.

34. The assay of claim 29, wherein the sulfonic acid polymer or salt thereof is present at a concentration of between 0.2 and 10% weight by volume.

35. The assay of claim 29, wherein the sulfonic acid polymer or salt thereof is present at a concentration of between 0.5 and 5% weight by volume.

36. The assay of claim 29, wherein the sulfonic acid polymer or salt thereof is present at a concentration of between 1 and 2.5% weight by volume.

37. The assay of claim 29, wherein the hybridizing conditions in steps (a) and (b) comprise a salt concentration in the range of 500 to 700 mM.

38. The assay of claim 29, wherein the label extender probe and/or capture extender probe concentration in step (a) is in the range of 1.5 to 2.5 nM.

39. The assay of claim 29, wherein the hybridizing conditions in steps (a) and (b) comprise a hybridization volume in the range of 40 to 60 uL.

40. The assay of claim 29, wherein the hybridizing conditions in steps (a) and (b) comprise a salt concentration in the range of 500 to 700 mM and a hybridization volume in the range of 40 to 60 uL; and the label extender probe and/or capture extender probe concentration in step (a) is in the range of 1.5 to 2.5 nM.

41. The assay of claim 40, wherein the sulfonic acid polymer or salt thereof is polyvinylsulfonic acid or a salt thereof.

42. The assay of claim 40, wherein the sulfonic acid polymer or salt thereof is polyanetholesulfonic acid or a salt thereof.

43. The assay of claim 29, wherein the sulfonic acid polymer or salt thereof has an average molecular weight in the range of from 1,000 to 2,000 Da.

44. The assay of claim 29, wherein the sulfonic acid polymer or salt thereof has an average molecular weight in the range of from 3,000 to 5,000 Da.

45. The assay of claim 29, wherein the sulfonic acid polymer or salt thereof has an average molecular weight in the range of from 5,000 to 7,000 Da.

46. The assay of claim 29, wherein the sulfonic acid polymer or salt thereof has an average molecular weight in the range of from 7,000 to 9,000 Da.

* * * * *